US005744464A

United States Patent [19]

Elger et al.

[11] Patent Number: 5,744,464
[45] Date of Patent: Apr. 28, 1998

[54] ANTIGESTAGENS FOR THE INHIBITION OF UTERINE SYNTHESIS OF PROSTAGLANDIN

[75] Inventors: Walter Elger; Krzysztof Chwalisz; Sybille Beier; Marianne Fahnrich, all of Berlin, Germany

[73] Assignee: Schering Aktiengesellschaft, Berlin, Germany

[21] Appl. No.: 96,360

[22] Filed: Jul. 26, 1993

Related U.S. Application Data

[63] Continuation of Ser. No. 581,444, Sep. 10, 1990, abandoned, which is a continuation of Ser. No. 100,682, Sep. 24, 1987, abandoned.

[30] Foreign Application Priority Data

Sep. 26, 1986 [DE] Germany .......................... 36 33 244.5

[51] Int. Cl.$^6$ .................................................. A61K 31/56
[52] U.S. Cl. .......................... 514/179; 514/180; 514/874; 514/899; 514/935
[58] Field of Search ............................... 514/179, 180, 514/899, 935, 874

[56] References Cited

U.S. PATENT DOCUMENTS

| | | | |
|---|---|---|---|
| 3,077,437 | 2/1963 | Heckel | 514/899 |
| 3,666,858 | 5/1972 | Hughes et al. | 514/179 |
| 4,609,651 | 9/1986 | Rohde et al. | 514/179 |
| 4,626,531 | 12/1986 | Elger et al. | 514/171 |
| 4,780,461 | 10/1988 | Neef et al. | 514/179 |
| 4,814,327 | 3/1989 | Ottow et al. | 514/182 |
| 4,870,069 | 9/1989 | Ottow et al. | 514/173 |

FOREIGN PATENT DOCUMENTS

| | | |
|---|---|---|
| 0139608 | 5/1985 | European Pat. Off. . |
| 0147361 | 7/1985 | European Pat. Off. . |

OTHER PUBLICATIONS

Fähnrich, Acta Endocrinol [Suppl], vol. 114 (Jun. 1987), p. 126.
Neulen et al., Acta Endocrinol [Suppl], vol. 114, 1987 (Jun. 2, 1987) pp. 7–8.
Pickles et al., J. Obstet. Gynecol. Br. Commonw., vol. 72,1965,pp. 185–192.
Willman et al., British Journal of Obstetrics and Gynaecology, vol. 83, No. 3, May 1976, pp. 337–341.
Maathuis et al., J. Endocr. (1978, 77, 361–371.
Elger et al., Am. J. Obstet. Gynecol., vol. 157 (4Pt2), 1987 Oct., pp. 1065–1074.
J. P. Wolf et al., "Progesterone antagonist (RU 486) for cervical . . . ", Am J Obstet Gynecol, Jan. 1989, pp. 45–47.
G. Haluska et al., "Temporal changes in uterine activity and . . . ", Am J Obstet Gynecol, Dec. 1987, pp. 1487–1495.
D.G. Porter, "The Failure of Porgesterone to Affect Myometrial . . . ", J. Endocr (1970), 46, 425–434.
Kettel et al., "Endocrine responses to long–term administration of . . . ", Gynecology–endocrinology, vol. 56, No. 3, Sep., 1991, pp. 402–407.
W. Elger, "Pharmacology of Parturition and Abortion", Anim Reprod Sci, 2 (1979) pp. 133–148.
W. Elger et al., "Studies on Labor–Conditioning and Labor–Inducing . . . ", Uterine Contractility, R. Garfield ed., Serono Symposia, USA, Uterine Contractility, R. Garfield ed., Serono Symposia, USA,.
W. Elger et al., "Studies on Interactions of Antiprogestins With . . . ", Hormone Antagonists for Fertility Regulation, C.P. Puri ed., pp. 105–121.
Shi Shai Qing et al., "PGFM and Sex Steroid Concentrations Throughout . . . ", Hormone Antagonists for Fertility Regulation, pp. 87–97.
W. Elger et al., "Studies on the Mechanism of Action of Antifertile . . . ", Acta Physiologica Hungarica, vol. 65(4), pp. 415–432 (1985).
W. Elger et al., "Endometrial and myometrail effects of progesterone . . . ", Am J Obstet Gynecol, vol. 157, No. 4, Oct. 1987, pp. 1065–1074.
R. Frydman et al., "Labor Induction in Women at Term With . . . ", Obstetrice & Gynecology, vol. 80, No. 6, pp. 972–975.
N.C.W. Hill et al., "Transplacental passage of mifepristone and its . . . ", Human Reproduction, vol. 6, No. 3, pp. 458–462, 1991.
L.M. Kettel et al., Society for Gynecologic Investigation Abstract, S136, "Lont–Term, Low–Dose RU 486 in the Treatment of Endometriosis".
The Merck Manual, Fifteenth Edition, pp. 1700–1713 (1987).
Baulieu et al, Human Reproduction, vol. 1, No. 2, pp. 107–110 (1986).

*Primary Examiner*—Ponnathapura Achutamurthy
*Attorney, Agent, or Firm*—Millen, White, Zelano & Branigan, P.C.

[57] ABSTRACT

Antigestagens inhibit prostaglandin synthesis by the uterus and thus can be used to treat symptoms of dysmennhorea.

23 Claims, No Drawings

ANTIGESTAGENS FOR THE INHIBITION OF UTERINE SYNTHESIS OF PROSTAGLANDIN

This application is a continuation, of application Ser. No. 07/581,444, filed Sept. 10, 1990, abandoned which is a continuation of application Ser. No. 07/100,682, filed Sep. 24, 1987, abandoned.

BACKGROUND OF THE INVENTION

The invention relates to the use of antigestagens and the production of drugs containing antigestagens for the inhibition of uterine synthesis of prostaglandin, especially for the treatment and prevention of dysmenorrheic symptoms.

Effective antigestagens are known, for example, from European patent specification 57,115 (Roussel-Uclaf).

Studied especially thoroughly was 11-beta-[4-N, N-dimethylamino)-phenyl]-17-beta-hydroxy-17-alpha-propinyl-4, 9(10)-estradien-3-one designated as RU 486. Data on the therapeutic mechanism of RU 486 are found in "Human Reproduction," Vol. 1 (1986), 107–110. According to it, antigestagen causes a blocking of progesterone activity and an increase of the formation of prostaglandin, and the prostaglandin stimulates uterine contractility. With RU 486, clinical studies to the end of pregnancy have just been conducted.

Prostaglandins play a key role in normal and pathological menstruation:

They are viewed in relation to changes in the blood supply of the mucous coating of the uterus and to the laborlike contractions of the uterus during menstruation. Increased release of PG and increased uterine contractions, which can be felt as extremely painful, are the essence of dysmenorrhea.

SUMMARY OF THE INVENTION

It is an object of the invention, therefore, to provide a method for the inhibition of dysmennorhea and prophalactic treatment of individuals with a history of such smyptons.

It has now been found that, contrary to the previous assumption, antigestagens inhibit uterine prodction of prostaglandins (PG). These objects therefore have been satisfied by the provision of a method for the use of antigestagens and the production of drugs containing antigestagens used in the inhibition of uterine synthesis of prostaglandin.

The invention further relates to the use of antigestagens for treatment and prevention of dysmenorrheic symptoms.

DETAILED DISCUSSION

Inhibition of uterine PG through the use of antigestagens eliminates or at least substantially lessens the symptoms which accompany dysmenorrhea. Since uterine synthesis of PG occurs essentially in the endometrium, disturbances and pains resulting from endometriosis will also be beneficially affected by antigestagens.

The inhibitory effect of antigestageus was observed in nonpregnant guinea pigs.

Luteolysis resulting from uterine PG at the end of the approximately 16-day cycle was blocked by antigestagens. A progression of serum progesterone values resulted which otherwise occurs only during pregnancy. Corresponding effects of inhibited uterine PG production would not be observed in human beings as a result of antigestagens, since in a woman the lifespan of the corpus luteum is not controlled by the uterus. However, with inhibition of uterine PG release in humans, a calming effect of the uterine motor system in the presence of dysmenorrhea will occur.

The advantage of this treatment course is that a desirable degree of inhibition is attained without affecting the PG function in other organs. A high degree of organ selectivity is achieved through the treatment of dysmenorrhea with antigestagens.

Antigestagens can be used at the onset of dysmenorrheic symptoms, such as "pains in the lower abdomen." It is sometimes appropriate to set the beginning of the treatment at somewhat earlier phases of the luteal phase to achieve a sufficient degree of inhibition. In such prophylactic treatment, typical hosts are those with a prior history of dysmenorrheic symptoms, and treatment is commenced before the onset of estrus or menstruation.

According to a preferred embodiment, the antigestagen treatment is given as a rule over 1 to 6, preferably 1 to 4 days, preferably starting at the beginning of the estrual or menstrual period or upon the appearance of symptoms.

As antigestagens, all compounds which have a strong affinity for the gestagen receptor (progesterone receptor) and at the same time show no gestagenic activity of their own are suitable. As competitive progesterone antagonists, the following steroids, for example, are suitable:

11-beta-[(4-N,N-dimethylamino)-phenyl]-17-beta-hydroxy-17-alpha-propinyl-4, 9(10)-estradien-3-one, 11-beta-[(4-N,N-dimethylamino)-phenyl]-17-beta-hydroxy-18-methyl-17-alpha-propinyl-4, 9(10)-estradien-3-one, 11-beta-[(4-N,N-dimethylamino)-phenyl]-17a-beta-hydroxy-17 a-alpha-propinyl-D-homo-4,9(10)-16-estratrien-3-one (European Patent Application 82400025.1-Publication Number 57,115), 11-beta-methoxyphenyl-17-beta-hydroxy-17-alpha-ethinyl-4, 9(10)-estradien-3-one, (Steroids 37 (1981) 361–382), 11-beta-[(4-N,N-dimethylamino)-phenyl]-17-beta-hydroxy-17-alpha-hydroxyprop-1-(Z)-enyl)-4, 9(10)-estradien-3-one (European Patent Application 847300147.0 -Publication Number 147,361), 11-beta-[(4-N, N-dimethylamino)-phenyl]-17-alpha-hydroxy-17-beta-(3-hydroxypropyl)-13-alpha-methyl-4,9(10-gonadien-3-one (European Patent Application 84730062.1-Publication Number 129,499). Other antigestagens which are disclosed in U.S. Pat. No. 4,536,401; U.S. application Ser. No. 077, 359, filed Jul. 24, 1987, U.S. application Ser. No. 827,050, filed Feb. 7, 1986 and U.S. application Ser. No. 832,604, filed Feb. 24, 1986, are useful.

The antigestagens can, for example, be administered locally, topically, enterally or parenterally.

For the preferred oral administration, particularly tablets, coated tablets, capsules, pills, suspensions or solutions which can be produced in the standard way with the admixtures and vehicles usual in galenic medicine are suitable. For local or topical use, vaginal suppositories or transdermal systems such as skin plasters, for example, are suitable.

According to the present invention, the antigestagens are used generally in amounts of about 2 to 50 mg/day, preferably about 5 to 20 mg/day of 11-beta-[(4-N,N-dimethylamino)-phenyl]-17-alpha-hydroxy-17-beta-(3-hydroxypropyl)-13-alpha-methyl-4, 9(10)-gonadien-3-one or in a biologically equivalent amount of another antigestagen. Such amounts can be routinely determined by differential dosage studies using a conventional protocol determining antigestagenic activity; e.g. *Fertility and Sterility* 40,253 (1982), *Steroids* 37, 361 (1981).

The compounds according to this invention when administered to patients, e.g., humans to inhibit PG formation or treat dysmenorrhea can be used analogously to the known agent Cyclo-Progynova ®. Dosage amounts are analogous when administered to prevent dysmenorrhea.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLE 1

Composition of a tablet with 10 mg of 11-beta-[(4-N,N-dimethylamino)-phenyl]-11-alpha-hydroxy-17-beta-(3-hydroxypropyl)-13-alpha-methyl-4,9(10)-gonadien-3-one for oral administration.

| | |
|---|---|
| 10.0 mg | 11-beta-[(4-N,N-dimethylamino)-phenyl]-17-alpha-hydroxy-17-beta-(3-hydroxypropyl)-13-alpha-methyl-4,9(10)-gonadien-3-one |
| 140.5 mg | lactose |
| 69.5 mg | corn starch |
| 2.5 mg | polyvinylpyrrolidone 25 |
| 2.0 mg | Aerosil |
| 0.5 mg | magnesium stearate |
| 225.0 mg | Total Weight |

EXAMPLE 2

Composition of an oily solution with 50 mg of 11-beta-[(4-N,N-dimethylamino)-phenyl]-17-alpha-hydroxy-17-beta-(3-hydroxypropyl)-13-alpha-methyl-4,9(10)-gonadien-3-one for parenteral administration.

50 mg of the antigestagen is dissolved in 1 ml each of castor oil/benzyl benzoate in a 6:4 ratio by volume.

EXAMPLE 3

Nonpregnant guinea pigs received daily, from the 8th to the 16th day of the approximately 16-day cycle, 10 mg of 11-beta-[(4-N,N-dimethylamino)-phenyl]-17-alpha-hydroxy-17-beta-(3-hydroxypropyl)-13-alpha-methyl-4,9(10)-gonadien-3-one. The test substance was dissolved in 1 ml of benzyl benzoate/castor oil (1:2) and injected subcutaneously. The progesterone content of the serum was determined daily.

It can be seen from the following table that the serum progesterone values for the animals treated with the antigestagen increase, while the serum progesterone values for the controls treated with solvent fall sharply toward the end of the cycle. Corresponding dose-dependent findings were obtained for this substance and also for other antigestagens in similar test arrangements. The increase of progesterone in the blood of animals treated with the antigestagen reflects an inhibition of uterine release of PG. Treatment of Nonpregnant Guinea Pigs with 10 mg of 11-beta-[(4-N,N-dimethylamino)-phenyl]-17-alpha-hydroxy-17-beta-(3-hydroxypropyl)-13-alpha-methyl-4,9(10)-gonadien-3-one

| | Animal No. | Progesterone/nmol/l serum | | | | |
|---|---|---|---|---|---|---|
| | | $d_0$ | $d_1$ | $d_4$ | $d_6$ | $d_8$ |
| Animals Treated With Anti-Gestagen | 6637 | 1.3 | 23.2 | 7.2 | 10.2 | 19.9 |
| | 6638 | 1.9 | 1.5 | 8.5 | 11.9 | 8.4 |
| | 6639 | 1.6 | 5.9 | 13.5 | 13.6 | 9.5 |
| | 6640 | 0.4 | 4.8 | 8.2 | 17.6 | 22.2 |
| Controls Treated With Solvent | 6641 | 0.4 | 6.1 | 5.3 | 7.1 | 8.0 |
| | 6642 | 3.7 | 2.3 | 11.7 | 8.7 | 18.1 |

| | | $d_{10}$ | $d_{12}$ | $d_{14}$ | $d_{15}$ | $d_{16}$ | $d_{17}$ |
|---|---|---|---|---|---|---|---|
| Animals Treated With Anti-Gestagen | 6637 | 20.5 | 18.8 | 10.2 | — | 16.0 | 26.8 |
| | 6638 | 14.3 | 16.1 | 17.4 | — | 25.6 | 24.6 |
| | 6639 | 13.0 | 13.0 | 24.2 | 18.4 | — | — |
| | 6640 | 23.6 | 36.0 | 31.4 | 39.8 | — | — |
| Controls Treated With Solvent | 6641 | 9.5 | 10.6 | 5.2 | — | 2.8 | 2.8 |
| | 6642 | 5.3 | 1.3 | 0.8 | 1.1 | — | — |

The preceding examples can be repeated with similar success by substituting the generically or specifically described reactants and/or operation conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the treatment of dysmenorrhea in a mammal, comprising treating dysmenorrhea by administering to the mammal host an effective amount of a steroidal antigestagen whereby uterine synthesis of prostaglandin is inhibited.

2. A method according to claim 1, wherein the antigestagen is
11-beta-[4-N,N-dimethylamino)-phenyl]-17-beta-hydroxy-17-alpha-propinyl-4,9(10)-estradien-3-one,
11-beta-[(4-N,N-dimethylamino)-phenyl]-17-beta-hydroxy-18-methyl-17-alpha-propinyl-4,9(10)-estradien-3-one,
11-beta-[(4-N,N-dimethylamino)-phenyl]-17a-beta-hydroxy-17a-alpha-propinyl-D-homo-4,9(10)-16-estratrien-3-one,
11-beta-methoxyphenyl-17-beta-hydroxy-17-alpha-ethinyl-4,9(10)-estradien-3-one,
11-beta-[(4-N,N-dimethylamino)-phenyl]-17-beta-hydroxy-17-alpha-hydroxyprop-1-(Z)-enyl)-4,9(10)-estradien-3one, or
11-beta-[(4-N,N-dimethylamino)-phenyl]-17-alpha-hydroxy-17-beta-(3-hydroxypropyl)-13-alpha-methyl-4,9 (10-gonadien-3-one.

3. A method according to claim 1, wherein the antigestagen is 11-beta-[(4-N,N-dimethylamino)-phenyl]-17-alpha-hydroxy-17-beta-(3-hydroxypropyl)-13-alpha-methyl-4,9(10)-gonadien-3-one.

4. A method according to claim 3, wherein the effective amount is about 2 to 50 mg/day.

5. A method according to claim 1, wherein the antigestagen is administered in an amount biologically equivalent to 2 to 50 mg/day of 11-beta-[(4-N, N-dimethylamino)- phenyl]-17-alpha-hydroxy-17-beta-(3-hydroxypropyl)-13-alpha-methyl-4,9(10)-gonadien-3-one.

6. A method according to claim 1, wherein the antigestagen is administered for a period of 1 to 6 days beginning at the onset of the estrual or menstrual period.

7. A method according to claim 1, wherein the host is a human.

8. A method for the treatment of dysmenorrheic symptoms in a female in need thereof, comprising administering to said female a steroidal antigestagen in an amount effective to alleviate said symptoms.

9. A method according to claim 8, wherein the antigestagen is administered for a period of 1 to 6 days beginning at the onset of the estrual or menstrual period.

10. A method according to claim 8, wherein the antigestagen is administered for a period of 1 to 4 days beginning at the onset of the estrual or menstrual period.

11. A method according to claim 8, wherein the antigestagen is
11-beta-[4-N,N-dimethylamino)-phenyl]-17-beta-hydroxy-17-alpha-propinyl-4,9(10)-estradien-3-one,
11-beta-[(4-N,N-dimethylamino)-phenyl]-17-beta-hydroxy-18-methyl-17-alpha-propinyl-4,9(10)-estradien-3-one,
11-beta-[(4-N,N-dimethylamino)-phenyl]-17a-beta-hydroxy-17a-alpha-propinyl-D-homo-4,9(10)-16-estratrien-3-one,
11-beta-methoxyphenyl-17-beta-hydroxy-17-alpha-ethinyl4, 9(10)-estradien-3-one,
11-beta-[(4-N,N-dimethylamino)-phenyl]-17-beta-hydroxy-17-alpha-hydroxyprop-1-(Z)-enyl]-4,9(10)-estradien-3-one, or
11-beta-[(4-N,N-dimethylamino)-phenyl]-17-alpha-hydroxy-17-beta-(3-hydroxypropyl)-13-alpha-methyl-4, 9(10-gonadien-3-one.

12. A method according to claim 8, wherein the antigestagen is 11-beta-[(4-N,N-dimethylamino)-phenyl]-17-alpha-hydroxy-17-beta-(3-hydroxypropyl)-13-alpha-methyl-4,9(10)-gonadien-3-one.

13. A method according to claim 12, wherein the antigestagen is administered in an amount of 2 to 50 mg/day.

14. A method according to claim 8, wherein the female is a human.

15. A method of preventing or prophylactically lessening dysmenorrheic symptoms in a female in need thereof, comprising before the onset of estrus or menstruation, administering an amount of a steroidal antigestagen effective to prevent or lessen said symptoms.

16. A method according to claim 15, wherein the antigestagen is
11-beta-[4-N,N-dimethylamino)-phenyl]-17-beta-hydroxy-17-alpha-propinyl-4,9(10)-estradien-3-one,
11-beta-[(4-N,N-dimethylamino)-phenyl]-17-beta-hydroxy-18-methyl-17-alpha-propinyl-4,9(10)-estradien-3-one,
11-beta-[(4-N,N-dimethylamino)-phenyl]-17a-beta-hydroxy-17a-alpha-propinyl-D-homo-4,9(10)-16-estratrien-3-one,
11-beta-methoxyphenyl-17-beta-hydroxy-17-alpha-ethinyl-4,9(10)-estradien-3-one,
11-beta-[(4-N,N-dimethylamino)-phenyl]-17-beta-hydroxy-17-alpha-hydroxyprop-1-(Z)-enyl]-4,9(10)-estradien-3one, or
11-beta-[(4-N,N-dimethylamino)-phenyl]-17-alpha-hydroxy-17-beta-(3-hydroxypropyl)-13-alpha-methyl-4,9 (10-gonadien-3-one.

17. A method according to claim 15, wherein the antigestagen is 11-beta-[(4-N,N-dimethylamino)-phenyl]-17-alpha-hydroxy-17-beta-(3-hydroxypropyl)-13-alpha-methyl-4, 9(10)-gonadien-3-one.

18. A method according to claim 15, wherein the female is a human.

19. A method for the treatment of endometriosis in a mammal, comprising treating endometriosis by administering to the mammal host an effective amount of a steroidal antigestagen whereby uterine synthesis of prostaglandin is inhibited.

20. A method for the treatment of primary dysmenorrhea in a mammal, comprising treating primary dysmenorrhea by administering to the mammal host an effective amount of a steroidal antigestagen whereby uterine synthesis of prostaglandin is inhibited.

21. A method for the treatment of secondary dysmenorrhea in a mammal, comprising treating secondary dysmenorrhea by administering to the mammal host an effective amount of a steroidal antigestagen whereby uterine synthesis of prostaglandin is inhibited.

22. A method according to claim 9, wherein the symptoms are resultant from primary dysmenorrhea.

23. A method for the treatment of pain associated with dysmenorrhea according to claim 9, comprising treating said pain by administering a steroidal antigestagen in an amount effective to alleviate said pain.

* * * * *